(12) United States Patent
Adler

(10) Patent No.: US 7,280,865 B2
(45) Date of Patent: Oct. 9, 2007

(54) ANCHORED FIDUCIAL APPARATUS AND METHOD

(75) Inventor: John R. Adler, Stanford, CA (US)

(73) Assignee: Accuray Incorporated, Sunnyvale, CA (US)

( * ) Notice: Subject to any disclaimer, the term of this patent is extended or adjusted under 35 U.S.C. 154(b) by 13 days.

(21) Appl. No.: 10/027,792

(22) Filed: Dec. 20, 2001

(65) Prior Publication Data

US 2003/0120141 A1    Jun. 26, 2003

(51) Int. Cl.
*A61B 5/05*    (2006.01)
(52) U.S. Cl. ............... 600/429; 600/425; 600/562; 600/414; 600/420; 600/424; 604/116; 606/130; 606/167; 606/185
(58) Field of Classification Search .............. 600/407, 600/426, 429, 414, 417, 437, 439, 431; 606/130
See application file for complete search history.

(56) References Cited

U.S. PATENT DOCUMENTS

| | | | |
|---|---|---|---|
| 5,271,415 A | 12/1993 | Foerster et al. | |
| 5,562,641 A * | 10/1996 | Flomenblit et al. | 604/531 |
| 5,902,310 A | 5/1999 | Foerster et al. | |
| 6,017,316 A | 1/2000 | Ritchart et al. | |
| 6,144,875 A * | 11/2000 | Schweikard et al. | 600/427 |
| 6,180,059 B1 | 1/2001 | Divino, Jr. et al. | |
| 6,203,568 B1 * | 3/2001 | Lombardi et al. | 623/1.13 |
| 6,228,055 B1 * | 5/2001 | Foerster et al. | 604/116 |
| 6,235,007 B1 | 5/2001 | Divino, Jr. et al. | |
| 6,248,087 B1 | 6/2001 | Spears et al. | |
| 6,261,243 B1 | 7/2001 | Burney et al. | |
| 6,296,659 B1 | 10/2001 | Foerster | |
| 6,356,782 B1 * | 3/2002 | Sirimanne et al. | 600/431 |
| 6,371,904 B1 * | 4/2002 | Sirimanne et al. | 600/3 |
| 6,454,997 B1 | 9/2002 | Divino, Jr. et al. | |
| 6,520,980 B1 | 2/2003 | Foerster | |
| 6,524,317 B1 | 2/2003 | Ritchart et al. | |
| 6,546,277 B1 | 4/2003 | Franck et al. | 600/426 |
| 6,547,800 B2 | 4/2003 | Foerster et al. | |
| 6,551,330 B1 | 4/2003 | Bain et al. | |
| 6,558,502 B2 | 5/2003 | Divino, Jr. et al. | |
| 6,582,453 B1 | 6/2003 | Tran et al. | |
| 6,585,730 B1 | 7/2003 | Foerster | |
| 6,607,698 B1 | 8/2003 | Spears et al. | |
| 6,660,008 B1 | 12/2003 | Foerster et al. | |
| 6,676,900 B1 | 1/2004 | Divino, Jr. et al. | |
| 6,746,417 B2 | 6/2004 | Spears et al. | |
| 6,770,076 B2 | 8/2004 | Foerster | |
| 6,780,198 B1 | 8/2004 | Gregoire et al. | |
| 6,855,157 B2 | 2/2005 | Foerster et al. | |
| 7,044,957 B2 | 5/2006 | Foerster et al. | |
| 7,083,638 B2 | 8/2006 | Foerster | |
| 7,090,690 B2 | 8/2006 | Foerster et al. | |
| 2004/0024304 A1 * | 2/2004 | Foerster et al. | 600/407 |

* cited by examiner

*Primary Examiner*—Eleni Mantis Mercader
*Assistant Examiner*—Parikha Mehta
(74) *Attorney, Agent, or Firm*—Blakely Sokoloff Taylor & Zafman LLP

(57) ABSTRACT

An anchored fiducial apparatus is described. The fiducial apparatus anchors itself in the target region once inserted so that the fiducial apparatus does not move relative to the target region.

27 Claims, 4 Drawing Sheets

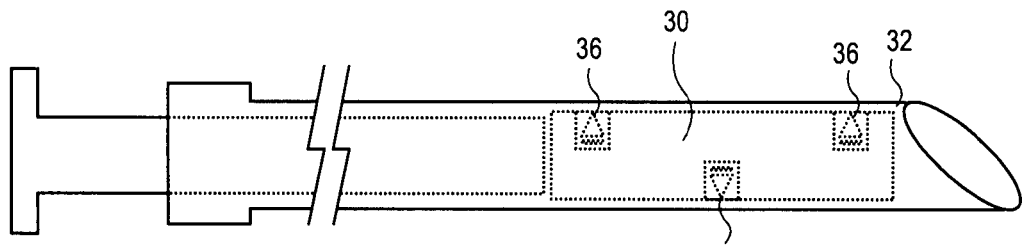
FIG. 1
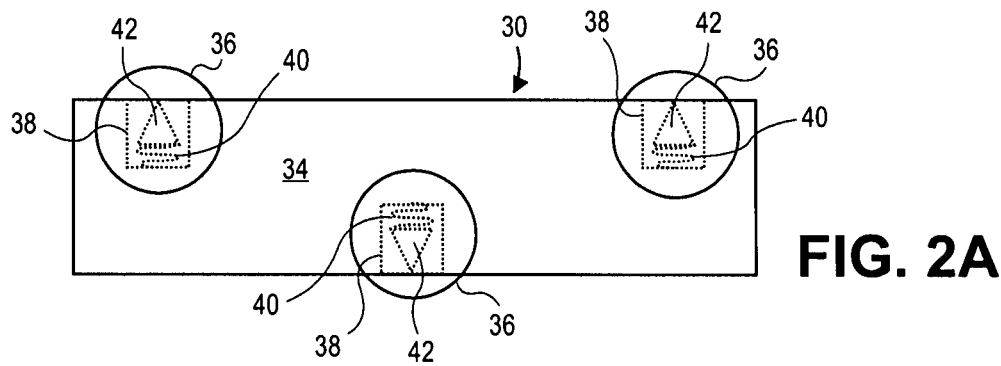
FIG. 2A
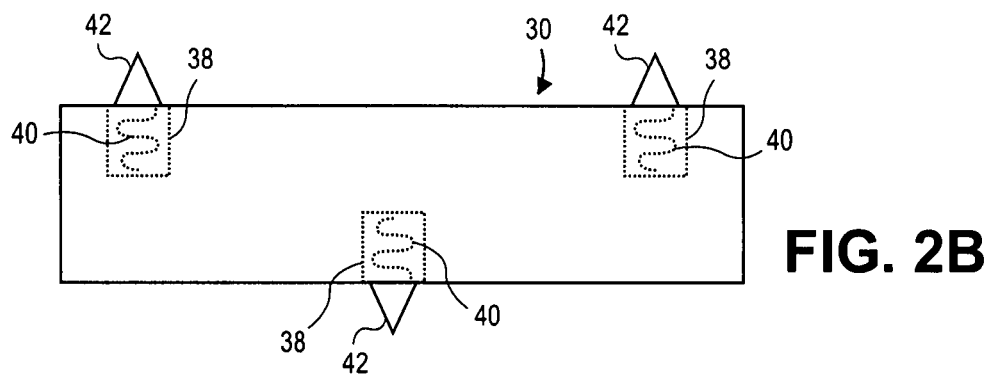
FIG. 2B
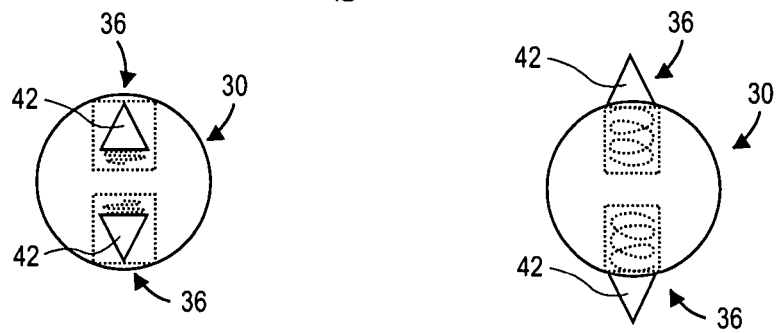
FIG. 3A
FIG. 3B

FIG. 5C        FIG. 5B

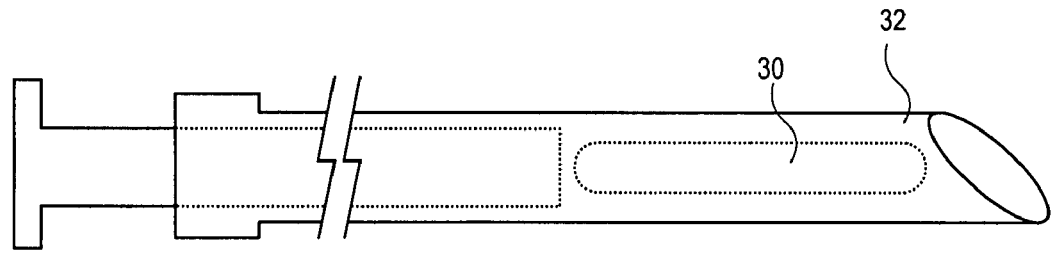
FIG. 6
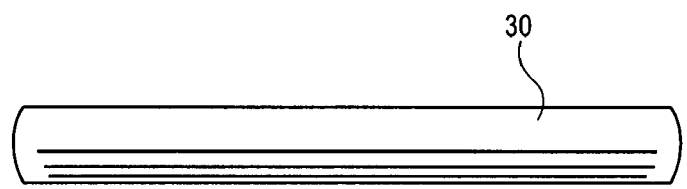
FIG. 7A
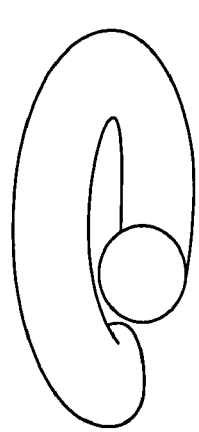 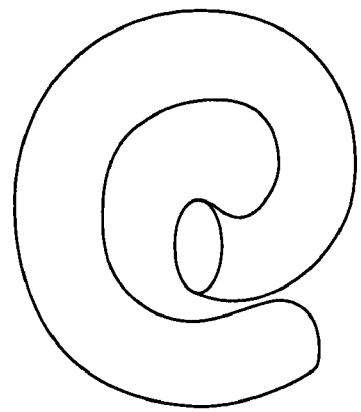
FIG. 7B     FIG. 7C

ANCHORED FIDUCIAL APPARATUS AND METHOD

BACKGROUND OF THE INVENTION

This invention relates generally to an apparatus and method for locating a particular portion of an object that is not viewable and in particular to an apparatus and method for locating a portion of an object by placing a marker that is viewable at or near the portion of the object.

In many applications, it is not possible to directly view an object or a portion of an object that needs to be acted on in some manner. For example, to treat a target region, such as a lung tumor, with radiation, it is not possible to be able to view the actual tumor within the patient immediately before the radiation treatment. It is therefore necessary to have some mechanism for permitting the lung tumor to be located accurately so that the radiation treatment can be targeted at the lung tumor while avoiding damage to healthy tissue.

In order to accurately track and target a target region, one or more fiducials may be used. Each fiducial is typically a substance that can be seen when an x-ray of the patient is viewed so that the lung tumor can be effectively located and targeted. Typically, the fiducials may be inserted into the patient during a simple operation. Each fiducial may be, for example, a radio-opaque substance that will be visible during an x-ray of the patient. These typical fiducials permit more accurate locating and targeting of the lung tumor, but there is a limit to the accuracy of targeting that can be achieved with these typical fiducials. In particular, the fiducials are normally placed into the lung tumor, but are not actually anchored to the lung tumor. Therefore, over time, the fiducials may move slightly or a large distance which makes the fiducials useless to locate the lung tumor and requires that new fiducials be inserted into the patient. It may actually be worse if the fiducials only move a small distance since the surgeon may not realize that the fiducials have moved and continue the treatment with bad targeting information (from the misaligned fiducials) that may lead to the radiation being delivered to the wrong location. In fact, the radiation may be delivered less effectively (in a smaller amount) to the lung tumor (which reduces the efficacy of the treatment) and delivered in a greater amount to the healthy tissue surrounding the lung tumor which will damage the healthy tissue and cause undesirable side effects.

To solve this problem, it is desirable to provide fiducials that may be anchored into a target region so that the fiducials are not able to move away from the target region and/or migrate. Thus, it is desirable to provide an anchored fiducial apparatus and it is to this end that the present invention is directed.

SUMMARY OF THE INVENTION

The anchored fiducial apparatus and method in accordance with the invention overcomes the limitations of the prior art fiducials. In particular, the anchored fiducials may be placed into a particular region to provide accurate location and tracking of that region. In one embodiment, the anchoring fiducial apparatus may be made of a radio opaque material that may be used to accurately locate a target region, such as a tumor, within a human patient during stereotaxic radiosurgery. The anchored fiducial apparatus in accordance with the invention anchors itself when it is placed into the region (of tissue) so that the anchored fiducial does not move/change its location relative to the region over time. The anchored fiducial apparatus may be inserted into the region by various well known techniques wherein the anchored fiducial is in an unanchored position during insertion into the region. Once the fiducial apparatus is inserted into the region, it may be placed into an anchored position in a state which secures/anchors the fiducial apparatus into the region (of tissue) and therefore unlikely to move and migrate over time as typical fiducials may.

The fiducial apparatus includes a body portion and one or more anchoring devices that anchor the fiducial apparatus into the region. In more detail, each anchoring device includes an elastic member and an anchor member. In two different embodiments, the anchor members have different shapes. In one embodiment, the anchor member is pyramidal shaped while in another embodiment the anchor member is an elongated rectangularly shaped member.

BRIEF DESCRIPTION OF THE DRAWINGS

FIG. 1 is a diagram illustrating a first embodiment of the fiducial apparatus in accordance with the invention and a method for inserting the fiducial into a target region;

FIG. 2a is a diagram illustrating the fiducial apparatus of FIG. 1 in an unanchored position;

FIG. 2b is a diagram illustrating the fiducial apparatus of FIG. 1 in an anchored position;

FIG. 3a illustrates an end view of the fiducial apparatus of FIG. 1 when in the unanchored position;

FIG. 3b illustrates an end view of the fiducial apparatus of FIG. 1 when in the anchored position;

FIG. 5b illustrates the fiducial of FIG. 4 in an anchored position;

FIG. 5c illustrates an end view of the fiducial of FIG. 4 when in the anchored position;

FIG. 6 is a diagram illustrating a third embodiment of the fiducial apparatus in accordance with the invention and a method for inserting the fiducial into a target region;

FIG. 7a illustrates the fiducial of FIG. 6 in an unanchored state;

FIGS. 7b and 7c illustrate the fiducial of FIG. 6 in an anchored state;

DETAILED DESCRIPTION OF A PREFERRED EMBODIMENT

Figure 4:
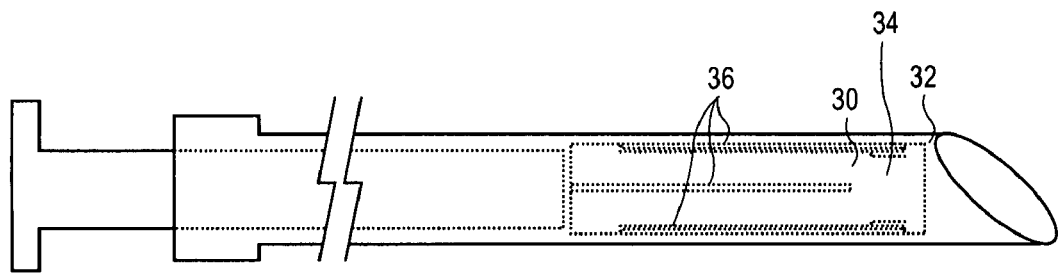
FIG. 4 is a diagram illustrating a second embodiment of the fiducial apparatus in accordance with the invention and a method for inserting the fiducial into a target region.

The invention is particularly applicable to a fiducial apparatus for locating a target region in a patient during surgery using electromagnetic radiation and it is in this context that the invention will be described. It will be appreciated, however, that the apparatus and method in accordance with the invention has greater utility since the described apparatus and method can be used to locate a portion of any object that is not readily viewable for a variety of different purposes. For example, the fiducial apparatus may be used for locating and targeting during other types of operations and medical procedures.

FIG. 1 is a diagram illustrating a preferred embodiment of the fiducial apparatus 30 in accordance with the invention and a method for inserting the fiducial into a target region. In this embodiment, the fiducial apparatus 30 may be inserted into a patient using a specific insertion needle 32 (also known as a needle with stylet or an "introducer" that "extrudes" the fiducial). In particular, the target region within the patient is identified, the needle attached to a syringe is inserted into the target region and the fiducial apparatus 30 is expelled from the tip of the needle as is well known. The invention is not limited to the particular insertion method shown since the fiducial apparatus 30 may be inserted into the patient or any object by any other well known technique, such as by surgical implantation. In this embodiment, the fiducial apparatus may have a round cross-section (as shown in FIGS. 3a and 3b) since it must pass through the needle of the syringe. However, the invention is not limited to any particular size or shape of the fiducial apparatus as long as the fiducial apparatus is sufficiently large to be viewed on an x-ray or any other similar imaging apparatus. In accordance with the invention, the fiducial apparatus may be made of any material which blocks the imaging energy so that the fiducial apparatus appears on an image generated by any typical imaging systems, such as x-rays. In a preferred embodiment, the fiducial apparatus may be made of a radio opaque material, such as gold. In other embodiments, the fiducial may be made of a material so that it is viewable in an ultrasound image so that it may be used as an ultrasound fiducial. Now, more details of this embodiment of the fiducial apparatus in accordance with the invention will be described.

FIG. 2a is a diagram illustrating the fiducial apparatus 30 of FIG. 1 in an unanchored position, FIG. 2b is a diagram illustrating the fiducial apparatus 30 of FIG. 1 in an anchored position, FIG. 3a illustrates an end view of the fiducial apparatus 30 of FIG. 1 when in the unanchored position and FIG. 3b illustrates an end view of the fiducial apparatus 30 of FIG. 1 when in the anchored position. As shown in FIGS. 2a and 2b, the fiducial apparatus may include a body portion 34 and one or more anchoring devices 36 embedded into the body portion. In the preferred embodiment, the anchoring devices 36 are located on opposite sides of the body portion as shown in FIGS. 3a and 3b, but the invention is not limited to any particular orientation of the anchoring devices 36 relative to one another.

Each anchoring device 36, in this embodiment, may include a housing portion 38 that houses an elastic member 40, such as a spring, and an anchor member 42 attached to the elastic member 40. In this embodiment, the anchor member is a spike that anchors itself into the target tissue. The spike may be pyramidal shape. The other end of the elastic member is attached to the body portion so that the elastic member urges the anchor member 42 outwards away from the body portion. Thus, as shown in FIG. 2b, once the fiducial apparatus exits the delivery mechanism, such as the needle of the syringe, so that the spring is no longer constrained, the anchor members 42 pop out from the body portion and embed themselves into the target region so that the fiducial apparatus does not move/change position or migrate. FIG. 2a and 3a illustrates the anchor members in a stored position while FIGS. 2b and 3b illustrate the anchor members in an anchoring state. Thus, the fiducial apparatus is anchored into its spot such that the accuracy of the location of the fiducial apparatus in the target region does not change over time as happens with typical unanchored fiducial apparatus. Now, another embodiment of the fiducial apparatus in accordance with the invention will be described.

FIG. 4 is a diagram illustrating a second embodiment of the fiducial apparatus 30 in accordance with the invention and a method for inserting the fiducial into a target region. In this embodiment, the fiducial apparatus 30 may be inserted into a patient using a needle 32. In particular, the target region within the patient is identified, the needle of the syringe is inserted into the target region and the fiducial apparatus 30 is expelled from the tip of the needle as is well known. The invention is not limited to the particular insertion method shown since the fiducial apparatus 30 may be inserted into the patient or any object by any other well known technique, such as by surgical implantation. In this embodiment, the fiducial apparatus may have a round cross-section (as shown in FIG. 5c) since it must pass through the needle of the syringe. However, the invention is not limited to any particular size or shape of the fiducial apparatus as long as the fiducial apparatus is sufficiently large to be viewed on an x-ray or any other similar imaging apparatus. In accordance with the invention, the fiducial apparatus may be made of any material which blocks the imaging energy so that the fiducial apparatus appears on an image generated by any typical imaging systems, such as x-rays. In a preferred embodiment, the fiducial apparatus may be made of a radio opaque material, such as gold. In other embodiments, the fiducial may be made of a material so that it is viewable in an ultrasound image so that it may be used as an ultrasound fiducial. Now, more details of this embodiment of the fiducial apparatus in accordance with the invention will be described.

Figure 5A:
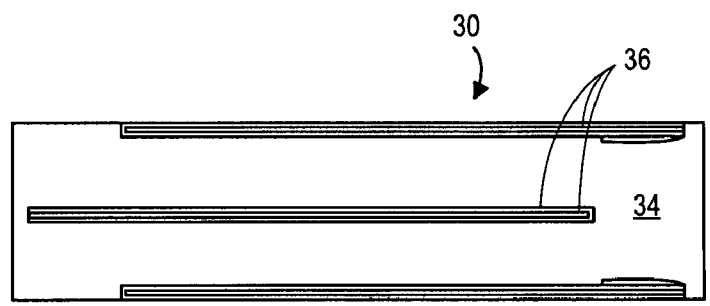
FIG. 5a illustrates the fiducial of FIG. 4 in an unanchored position.
Figure 5D:
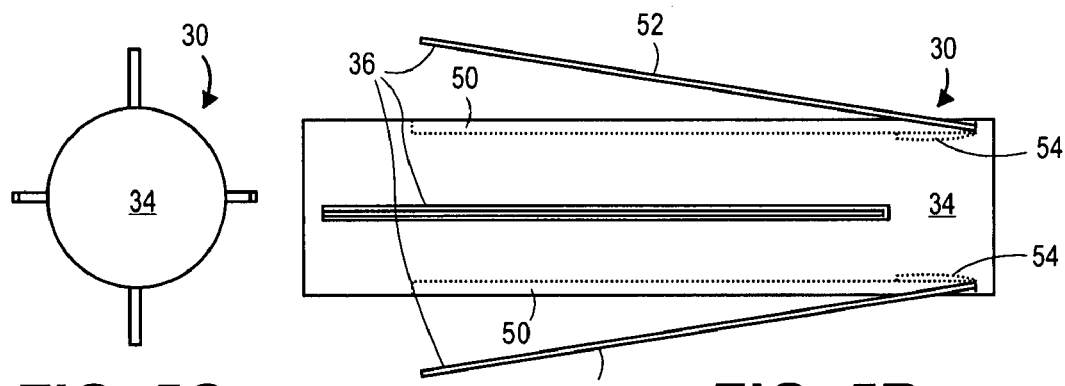
FIG. 5d illustrates another view of the fiducial of FIG. 4 when in the anchored position.
Figure 5D:
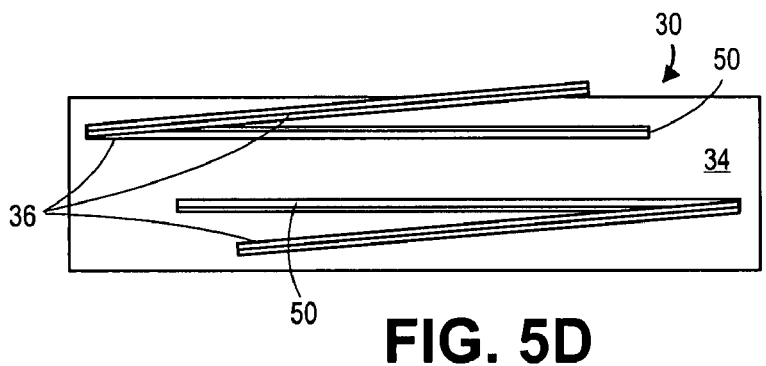

In particular, FIG. 5a illustrates the fiducial 30 of FIG. 4 in an unanchored position, FIG. 5b illustrates the fiducial 30 of FIG. 4 in an anchored position, FIG. 5c illustrates an end view of the fiducial 30 of FIG. 4 when in the anchored position and FIG. 5d illustrates another view of the fiducial 30 of FIG. 4 when in the anchored position. As shown in FIGS. 5a and 5b, the fiducial apparatus may include a body portion 34 and one or more anchoring devices 36 embedded into the body portion. In the preferred embodiment, the anchoring devices 36 are located on opposite sides of the body portion as shown in FIG. 5c, but the invention is not limited to any particular orientation of the anchoring devices 36 relative to one another.

Each anchoring device 36, in this embodiment, may include a housing portion 50 (a trench in this embodiment) that houses an anchor member 52 and an elastic member 54, such as a spring, wherein the anchor member is attached to the elastic member. In this embodiment, the anchor member is an elongated rectangular shaped member anchored at one end so that as it is released from the housing portion, it anchors itself into the target region (See FIG. 5b). The other end of the elastic member is attached to the body portion so that the elastic member urges the anchor member 52 outwards away from the body portion when the anchor member is released. Thus, as shown in FIG. 5b, once the fiducial apparatus 30 exits the delivery mechanism, such as the needle of the syringe, so that the elastic member is no longer constrained, the anchor members 52 pop out from the body portion and embed themselves into the target region so that the fiducial apparatus does not move/change position or migrate. FIG. 5a illustrates the anchor members in a stored position while FIGS. 5b-5d illustrate the anchor members in an anchoring state. Thus, the fiducial apparatus is anchored into its spot such that the accuracy of the location of the fiducial apparatus in the target region does not change over time as happens with typical unanchored fiducial apparatus. Now, another embodiment of the fiducial apparatus will be described.

FIG. 6 is a diagram illustrating a third embodiment of the fiducial apparatus 30 in accordance with the invention and a method for inserting the fiducial into a target region. In this embodiment, the fiducial apparatus 30 may be inserted into a patient using a needle and syringe 32. In particular, the target region within the patient is identified, the needle of the syringe is inserted into the target region and the fiducial apparatus 30 is expelled from the tip of the needle as is well known. The invention is not limited to the particular insertion method shown since the fiducial apparatus 30 may be inserted into the patient or any object by any other well known technique, such as by surgical implantation. In this embodiment, the fiducial apparatus may have a round cross-section (as shown in FIGS. 7b and 7c) since it must pass through the needle of the syringe. However, the invention is not limited to any particular size or shape of the fiducial apparatus as long as the fiducial apparatus is sufficiently large to be viewed on an x-ray or any other similar imaging apparatus. In accordance with the invention, the fiducial apparatus may be made of any material which blocks the imaging energy so that the fiducial apparatus appears on an image generated by any typical imaging systems, such as x-rays. In a preferred embodiment, the fiducial apparatus may be made of a radio opaque material. In other embodiments, the fiducial may be made of a material so that it is viewable in an ultrasound image so that it may be used as an ultrasound fiducial. Now, more details of this embodiment of the fiducial apparatus in accordance with the invention will be described. an image generated by any typical imaging systems, such as x-rays. In a preferred embodiment, the fiducial apparatus may be made of a radio opaque material. In other embodiments, the fiducial may be made of a material so that is may be used as a ultrasound fiducial. Now, more details of this embodiment of the fiducial apparatus in accordance with the invention will be described.

In particular, FIG. 7a illustrates the fiducial 30 of FIG. 6 in an unanchored state and FIGS. 7b and 7c illustrate the fiducial 30 of FIG. 6 in an anchored state. In this embodiment, the fiducial apparatus is made out of a memory metallic substance, such as nitinol, which reacts to an electric field by bending as is well known. The fiducial apparatus may also be made of a material that is temperature sensitive and bends in response to a particular temperature range, such as the temperature within the human body. Thus, as shown in FIG. 7a, an electric field is applied during the insertion of the fiducial apparatus so that the fiducial apparatus remains relatively straight. As shown in FIGS. 7b and 7c, once the adjacent electric field is removed and does not interact with the fiducial apparatus, the fiducial apparatus bends so that it is less likely to move within the target region.

Figure 8:
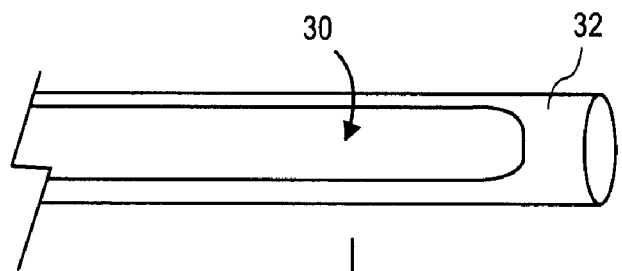
FIG. 8 illustrates another embodiment of the fiducial in accordance with the invention.

FIG. 8 illustrates another embodiment of the fiducial apparatus 30 in accordance with the invention and a method for inserting the fiducial into a target region. In this embodiment, the fiducial apparatus 30 may be inserted into a patient using a needle 32. In particular, the target region within the patient is identified, the needle of the syringe is inserted into the target region and the fiducial apparatus 30 is expelled from the tip of the needle as is well known. The invention is not limited to the particular insertion method shown since the fiducial apparatus 30 may be inserted into the patient or any object by any other well known technique, such as by surgical implantation. In this embodiment, the fiducial apparatus may have a round cross-section since it must pass through the needle of the syringe. However, the invention is not limited to any particular size or shape of the fiducial apparatus as long as the fiducial apparatus is sufficiently large to be viewed on an x-ray or any other similar imaging apparatus. In accordance with the invention, the fiducial apparatus may be made of any material which blocks the imaging energy so that the fiducial apparatus appears on an image generated by any typical imaging systems, such as x-rays. In a preferred embodiment, the fiducial apparatus may be made of a radio opaque material. In other embodiments, the fiducial may be made of a material so that it is viewable in an ultrasound image so that it may be used as an ultrasound fiducial. Now, more details of this embodiment of the fiducial apparatus in accordance with the invention will be described.

Figure 9A:
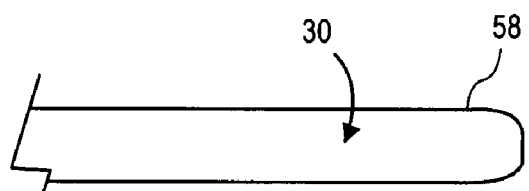
FIGS. 9A and 9B illustrate the fiducial of FIG. 8 in an unanchored state and in an anchored state, respectively.
Figure 9B:
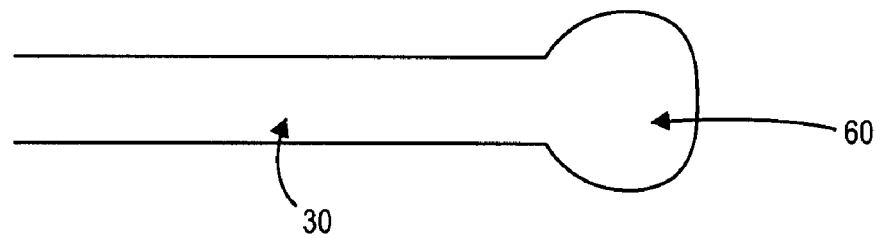

FIGS. 9A and 9B illustrate the fiducial of FIG. 8 in an unanchored state and in an anchored state, respectively. In this embodiment, the fiducial apparatus may include an elastic body portion 58 that may be stretched by the insertion of a fluid or other material into the body portion 58. As shown in FIG. 9A, when the fiducial apparatus is in the unanchored state, the body portion 5Sis empty. To put the fiducial apparatus into the anchored state, a fluid or other material 60 is inserted into the body portion 58 that expands as shown to anchor the fiducial into the target region. As with the other embodiments, the fluid may be a radio opaque material or an ultrasound opaque material.

While the foregoing has been with reference to a particular embodiment of the invention, it will be appreciated by those skilled in the art that changes in this embodiment may be made without departing from the principles and spirit of the invention, the scope of which is defined by the appended claims.

The invention claimed is:

1. A method, comprising:
   depositing a fiducial into a target region of a patient, wherein the fiducial comprises a body portion and an anchor member coupled to the body portion, the body portion having a housing, the anchor member drawn into the housing in an unanchored position;
   anchoring the fiducial into the target region of the patient, wherein the anchor member is withdrawn from the housing in an anchored position, wherein anchoring comprises penetrating tissue near the target region with the anchor member;
   detecting the fiducial using electromagnetic radiation to locate the target region of the patient; and
   performing stereotaxic radiosurgery on the target region of the patient according to the detected fiducial and the location of the target region.

2. The method of claim 1, further comprising tracking the target region during the stereotaxic radiosurgery.

3. The method of claim 1, further comprising applying radiation treatment to the target region.

4. The method of claim 1, wherein detecting the fiducial comprises viewing the fiducial using an x-ray imager, wherein the fiducial comprises a radiopaque material.

5. The method of claim 1, wherein detecting the fiducial comprises viewing the fiducial using an ultrasonic imager, wherein the fiducial comprises an ultrasonic opaque material.

6. A fiducial apparatus, comprising:
   a body portion having a housing, the body portion comprising a material visible using electromagnetic radiation; and
   an anchor member coupled to the body portion, the anchor member having an unanchored position and an anchored position, the anchor member drawn into the housing in the unanchored position and withdrawn from the housing in the anchored position to penetrate tissue at a treatment region.

7. The apparatus of claim 6, further comprising an elastic member coupled to the anchor member and the body portion, the elastic member to urge the anchor member from the unanchored position to the anchored position.

8. The apparatus of claim 7, wherein the elastic member comprises a spring coupled between the anchor member and the body portion to urge the anchor member to withdraw from the housing.

9. The apparatus of claim 7, wherein the anchor member comprises a pyramidal spike to embed into a target region.

10. The apparatus of claim 7, wherein the anchor member comprises an elongated rectangular shaped member.

11. The apparatus of claim 10, wherein the elongated rectangular shaped member comprises a first end and a second end, the elastic member coupled to the elongated rectangular shaped member at the first end to urge the second end away from the body portion.

12. The apparatus of claim 6, wherein the body portion comprises a memory metal member that bends in response to a presence or an absence of an appropriate signal.

13. The apparatus of claim 12, wherein the appropriate signal comprises an electromagnetic signal or an ambient temperature.

14. The apparatus of claim 6, wherein the material comprises an ultrasonic opaque material visible using an ultrasonic imager.

15. The apparatus of claim 6, wherein the material comprises a radiopaque material visible using an x-ray imager.

16. A method, comprising:
 inserting an insertion needle into a tissue target region of a patient, the insertion needle containing a fiducial in an unanchored position, the fiducial comprising a body portion and an anchor member coupled to the body portion, the body portion having a housing, the anchor member drawn into the housing in the unanchored position;
 displacing a portion of the tissue target region;
 depositing the fiducial into the tissue target region; and
 penetrating tissue with the anchor member at the tissue target region by withdrawing the anchor member from the housing in response to the fiducial exiting the insertion needle.

17. The method of claim 16, further comprising moving the anchor member from the unanchored position to an anchored position withdrawn from the housing.

18. The method of claim 16, further comprising using an ultrasonic imager to view the deposited fiducial.

19. The method of claim 16, further comprising using an x-ray imager to view the deposited fiducial.

20. The method of claim 16, further comprising applying an electromagnetic signal to the fiducial to maintain the fiducial in the unanchored position during insertion into the tissue target region, wherein the fiducial comprises a memory metal member that bends in response to a presence or an absence of the electromagnetic signal.

21. The method of claim 16, wherein the tissue target region comprises a tumor.

22. A fiducial apparatus, comprising:
 means for displacing a portion of a tissue target region, the means for displacing comprising a body portion having a housing; and
 means for penetrating tissue at the tissue target region, the means for penetrating being drawn into the housing in an unanchored position and withdrawn from the housing in an anchored position.

23. The apparatus of claim 22, means for urging the anchor member from the unanchored position to the anchored position.

24. The apparatus of claim 22, further comprising means for viewing the fiducial within the tissue target region using an ultrasonic imager.

25. The apparatus of claim 22, further comprising means for viewing the fiducial within the tissue target region using an x-ray imager.

26. The apparatus of claim 22, wherein the tissue target region comprises a tumor.

27. A fiducial apparatus, comprising:
 a body portion having a housing, the body portion comprising a material visible using electromagnetic radiation, the housing comprising a trench in the body portion;
 an elastic member in the housing and coupled to the body portion; and
 an anchor member coupled to the elastic member, the anchor member having an unanchored position and an anchored position, the anchor member drawn into the housing in the unanchored position and at least a portion of the anchor member released from the housing in the anchored position to penetrate tissue at a treatment region, the elastic member urging the anchor member away from the body portion in the anchored position.

* * * * *